United States Patent
Ito

(10) Patent No.: US 10,156,616 B2
(45) Date of Patent: Dec. 18, 2018

(54) NUCLEAR MAGNETIC RESONANCE IMAGING APPARATUS AND RF SHIMMING METHOD

(71) Applicant: HITACHI, LTD., Tokyo (JP)

(72) Inventor: Kosuke Ito, Tokyo (JP)

(73) Assignee: HITACHI, LTD., Tokyo (JP)

( * ) Notice: Subject to any disclaimer, the term of this patent is extended or adjusted under 35 U.S.C. 154(b) by 84 days.

(21) Appl. No.: 15/127,866

(22) PCT Filed: Mar. 25, 2015

(86) PCT No.: PCT/JP2015/059032
§ 371 (c)(1),
(2) Date: Sep. 21, 2016

(87) PCT Pub. No.: WO2015/159664
PCT Pub. Date: Oct. 22, 2015

(65) Prior Publication Data
US 2017/0108564 A1    Apr. 20, 2017

(30) Foreign Application Priority Data

Apr. 16, 2014  (JP) ................................ 2014-084603

(51) Int. Cl.
*G01R 33/36* (2006.01)
*A61B 5/055* (2006.01)
(Continued)

(52) U.S. Cl.
CPC .......... *G01R 33/3607* (2013.01); *A61B 5/055* (2013.01); *G01R 33/288* (2013.01); *G01R 33/5659* (2013.01)

(58) Field of Classification Search
None
See application file for complete search history.

(56) References Cited

U.S. PATENT DOCUMENTS

2005/0231203 A1  10/2005  Feiweier et al.
2008/0100292 A1  5/2008   Hancu
(Continued)

FOREIGN PATENT DOCUMENTS

CN    102159966 A    8/2011
JP    2012-502683    2/2012
(Continued)

OTHER PUBLICATIONS

International Search Report in connection with PCT/JP2015/059032.
E.A.Attardo et al. "Field Synthesis in Inhomogeneous Media: Joint Control of Polarization, Uniformity and SAR in MRI $B_1$-Field", Progress In Electromagnetics Research, vol. 118, pp. 355-377, 2011.
(Continued)

*Primary Examiner* — Paresh H Patel
(74) *Attorney, Agent, or Firm* — Cooper & Dunham LLP

(57) ABSTRACT

The present invention provides an RF shimming method for a nuclear magnetic resonance imaging apparatus comprising: a transmission coil having a plurality of channels that respectively transmit high frequencies to an object and a calculation unit performing RF shimming calculation that determines at least one of amplitudes and phases of the high frequencies to be transmitted respectively to a plurality of the channels so as to improve homogeneity of a high-frequency magnetic field distribution generated by the transmission coil and reduce a specific absorption ratio of the object. Objective function parameters for setting the objective function are determined according to contribution to the SAR for each of the channels during the RF shimming calculation based on the objective function and the restriction condition.

10 Claims, 10 Drawing Sheets

| OBJECTIVE FUNCTION PARAMETERS | BREAST | RIGHT SHOULDER/ARM | LEFT SHOULDER/ARM |
|---|---|---|---|
| DISTRIBUTION WEIGHT (w) | 0.5 | 0.5 | 0.5 |
| AMPLITUDE EXPONENT (k) | 2 | 2 | 2 |
| WEIGHT OF CHANNEL 1 | 1.6 | 0.4 | 1.6 |
| WEIGHT OF CHANNEL 2 | 0.4 | 0.4 | 1.6 |
| WEIGHT OF CHANNEL 3 | 0.4 | 1.6 | 0.4 |
| WEIGHT OF CHANNEL 4 | 1.6 | 1.6 | 0.4 |

(51) Int. Cl.
  *G01R 33/28* (2006.01)
  *G01R 33/565* (2006.01)

(56) References Cited

U.S. PATENT DOCUMENTS

| | | | |
|---|---|---|---|
| 2008/0129298 A1* | 6/2008 | Vaughan | G01R 33/5612 324/322 |
| 2008/0238425 A1 | 10/2008 | Xu et al. | |
| 2010/0253344 A1 | 10/2010 | Fautz | |
| 2010/0301859 A1 | 12/2010 | Boulant | |
| 2011/0156704 A1* | 6/2011 | Boernert | G01R 33/3415 324/309 |
| 2013/0251227 A1 | 9/2013 | Wang et al. | |

FOREIGN PATENT DOCUMENTS

| | | |
|---|---|---|
| JP | 2013-505046 | 2/2013 |
| WO | WO 2014/021172 A1 | 2/2014 |

OTHER PUBLICATIONS

Lin Tang et al. "Studies of RF Shimming Techniques with Minimization of RF Power Deposition and Their Associated Temperature Changes", Concepts Magn Reson Part B Magn Reson Eng. pp. 1-25, 2011.

P. Balchandani et al. "Adiabatic B1 Shimming Algorithm for Multiple Channel Transmit at 7T" Proc. Intl. Soc. Mag: Reson. Med. 19. p. 2907, 2011.

B. Van Den Bergen, "7 T Body MRI: B1 Shimming with Simultaneous SAR Reduction," Physics in Medicine and Biology, V.52 N. 17, pp. 5429-5441 (Sep. 7, 2007).

R. Lattanzi et al. "Electrodynamic analysis of SAR and transmit homogeneity for RF shimming on a dielectric cylinder" Proc. Intl. Soc. Mag. Reson. Med. 17. p. 4510, 2009.

Chinese official action dated Aug. 29, 2018 in corresponding Chinese Patent Application No. 201580010607.0.

* cited by examiner

FIG.2
(A) 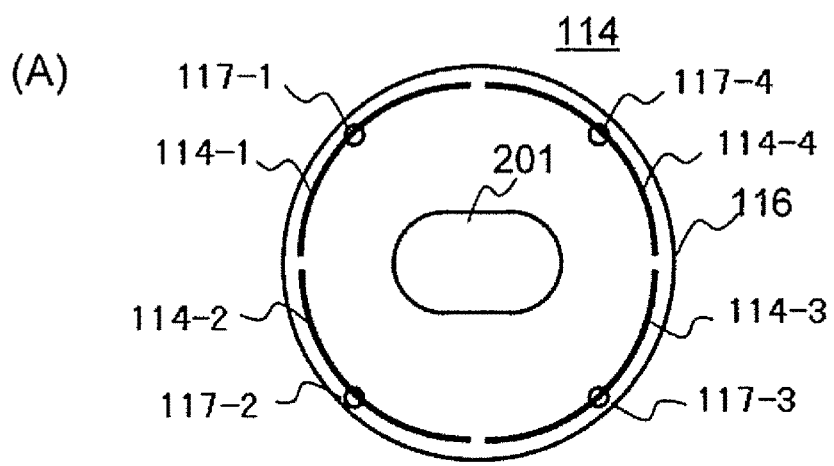
(B) 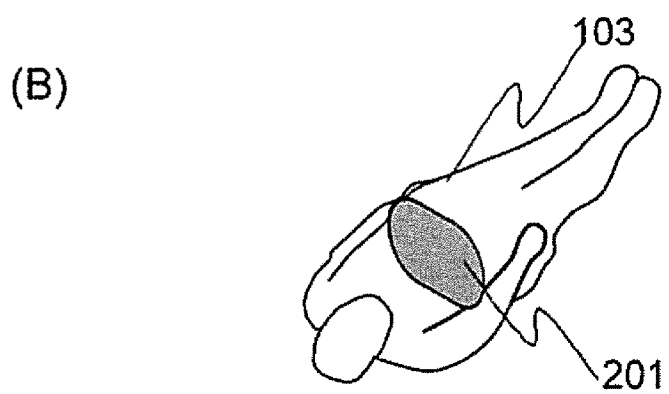
(C) 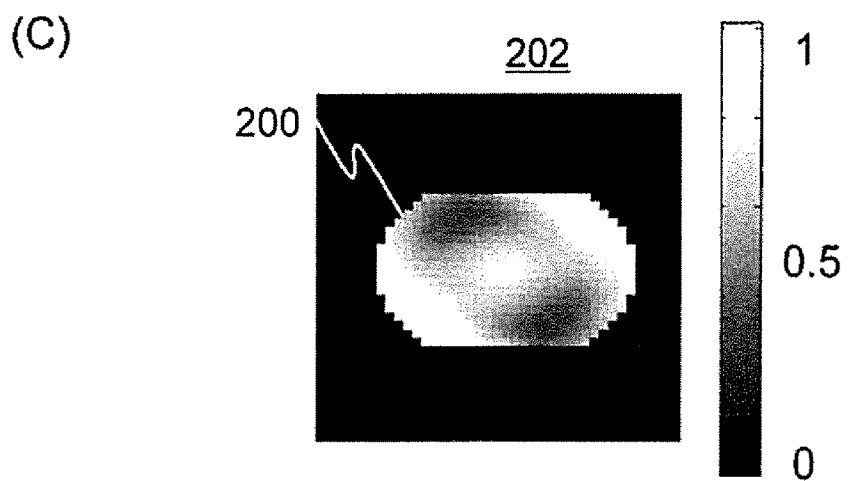

FIG.7
(A)
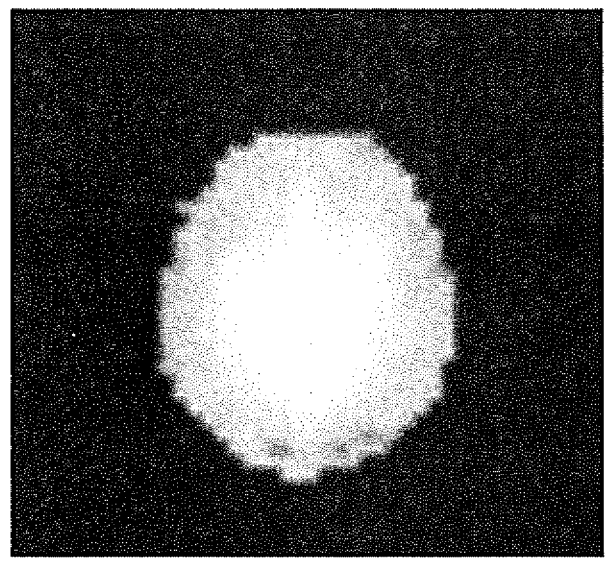
(B)
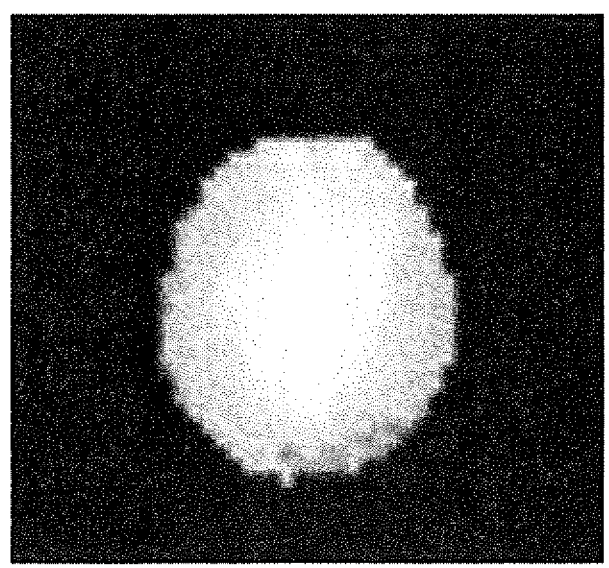

FIG.8

| OBJECTIVE FUNCTION PARAMETERS | BREAST | RIGHT SHOULDER/ARM | LEFT SHOULDER/ARM |
|---|---|---|---|
| DISTRIBUTION WEIGHT (w) | 0.5 | 0.5 | 0.5 |
| AMPLITUDE EXPONENT (k) | 2 | 2 | 2 |
| WEIGHT OF CHANNEL 1 | 1.6 | 0.4 | 1.6 |
| WEIGHT OF CHANNEL 2 | 0.4 | 0.4 | 1.6 |
| WEIGHT OF CHANNEL 3 | 0.4 | 1.6 | 0.4 |
| WEIGHT OF CHANNEL 4 | 1.6 | 1.6 | 0.4 |

NUCLEAR MAGNETIC RESONANCE IMAGING APPARATUS AND RF SHIMMING METHOD

TECHNICAL FIELD

The present invention relates to a nuclear magnetic resonance imaging (MRI) technique, and, in particular, to homogeneity improvement of high-frequency magnetic fields to be irradiated by a multi-channel transmission coil and SAR (Specific Absorption Ratio) reduction of an object.

BACKGROUND ART

An MRI apparatus is a medical image diagnostic apparatus that causes nuclear magnetic resonance to atomic nuclei in an arbitrary cross section across an object to acquire a tomographic image in the cross section from nuclear magnetic resonance signals to be generated. A radio frequency (hereinafter, referred to as RF) wave that is a type of electromagnetic wave is transmitted to the object to excite spins of the atomic nuclei in the object, and then the nuclear magnetic resonance signals to be generated by the atomic spins are received to generate an image of the object. The RF transmission to the object is performed by an RF transmission coil, and the nuclear magnetic resonance signal reception from the object is performed by an RF reception coil.

A static magnetic field strength tends to be larger in order to improve an SNR (Signal to Noise Ratio) of an image, and a high magnetic field MRI apparatus (ultra-high magnetic field MRI apparatus) whose static magnetic field strength is equal to or more than 3T (Tesla) has prevailed recently. However, the larger the static magnetic field strength becomes, the more the SNR is improved, which can easily cause unevenness in the generated image. This is because an RF frequency to be used for exciting a nuclear magnetic resonance phenomenon is increased by a higher magnetic field.

For example, a 128-MHz RF is used for an MRI apparatus whose static magnetic field strength is equal to or more than 3T (Tesla) (hereinafter, referred to as a 3T MRI apparatus). The RF wavelength is approximately 30 cm that is almost the same scale as an abdominal cross section in the biological body, and a change occurs in the phase. An inhomogeneous spatial distribution is generated in a rotating magnetic field (hereinafter, referred to as a high-frequency magnetic field: $B_1$) generated by an RF and a nuclear magnetic resonance phenomenon excited by the RF due to the change in the phase, which causes image unevenness. Therefore, a technique to reduce the inhomogeneity of the spatial distribution in the high-frequency magnetic field $B_1$ is required for RF irradiation to be executed in an ultra-high magnetic field MRI apparatus.

An RF irradiation method referred to as "RF shimming" is used to reduce inhomogeneity of a $B_1$ distribution. This method reduces $B_1$ inhomogeneity in an imaging region by using an RF transmission coil having a plurality of channels to control a phase and an amplitude of an RF signal to be provided to each channel (for example, refer to Patent Literature 1). A $B_1$ distribution of each channel is measured previously before main imaging, and the amplitude and the phase of an RF pulse appropriate for each of the channels are calculated in order to reduce the $B_1$ inhomogeneity using the $B_1$ distribution. At this time, a region that is a part of a cross section and should be diagnosed is set as a region of interest (ROI), and the amplitude and the phase of the RF pulse for each of the channels are determined so as to reduce the $B_1$ inhomogeneity in the ROI (for example, refer to Patent Literature 2).

CITATION LIST

Patent Literature

PTL 1: Description of U.S. Pat. No. 7,078,901
PTL 2: International Publication No. 2014/021172

SUMMARY OF INVENTION

Technical Problem

In an MRI apparatus with a higher magnetic field, considering the safety of a biological body, an RF specific absorption ratio in the biological body is regulated so as to fall within a predetermined range. However, as the magnetic field of the apparatus becomes higher, an RF frequency to be used increases, which also increases an SAR.

In RF shimming described in PTL 2, objective function parameter values for setting an objective function are determined according to the contribution to an SAR when calculation of the RF shimming is performed based on the objective function and a restriction condition. However, in a case of a transmission coil having a plurality of channels, the contribution to the SAR for each of the channels differs depending on the distance to the object and the imaging conditions. Because this is not considered in the method of PTL 2, the SAR can be further reduced while a $B_1$ distribution is being homogenized.

Therefore, the present invention was made in light of the above circumstances and has a purpose to reduce a SAR according to contribution to the SAR for each of the channels while homogenizing a $B_1$ distribution during RF shimming calculation based on an objective function and a restriction condition in an MRI apparatus that uses a transmission coil having a plurality of channels.

Solution to Problem

The present invention is configured as follows in order to solve the above problems. That is, the present invention is an RF shimming method for a nuclear magnetic resonance imaging apparatus comprising: a transmission coil having a plurality of channels that respectively transmit high frequencies to an object and a calculation unit performing RF shimming calculation that determines at least one of amplitudes and phases of the high frequencies to be transmitted respectively to a plurality of the channels so as to improve homogeneity of a high-frequency magnetic field distribution generated by the transmission coil and to reduce a specific absorption ratio of the object. Objective function parameter values for setting the objective function are determined according to contribution to the SAR for each of the channels during the RF shimming calculation based on the objective function and the restriction condition.

Advantageous Effects of Invention

According to the present invention, a SAR can be reduced according to contribution to the SAR for each of the channels while homogenizing a $B_1$ distribution during RF shimming calculation based on an objective function and a restriction condition in an MRI apparatus that uses a transmission coil having a plurality of channels.

BRIEF DESCRIPTION OF DRAWINGS

FIG. 2(A) is an explanatory view illustrating a transmission coil of an embodiment of the present invention; FIG. 2(B) is an explanatory view illustrating an imaging region of an embodiment of the present invention; and FIG. 2(C) is an explanatory view illustrating a simulation result of the distribution of a rotating magnetic field $B_1$ to be generated in a phantom of an embodiment of the present invention.

FIG. 7 is a specific example of the first embodiment, in which imaging is performed using a four-channel transmission coil as illustrated in FIG. 2(A), and shows a measurement result of a $B_1$ map of the entire FOV.

FIG. 8 is a specific example of a second embodiment and shows an example of objective function parameter values for each of the imaging sites.

DESCRIPTION OF EMBODIMENTS

Hereinafter, embodiments to which the present invention is applied will be described using drawings. It is noted that the same reference sign is provided for the same function in all the drawings for explaining each embodiment, and the repeated description will be omitted. This does not limit the present invention.

Figure 1:
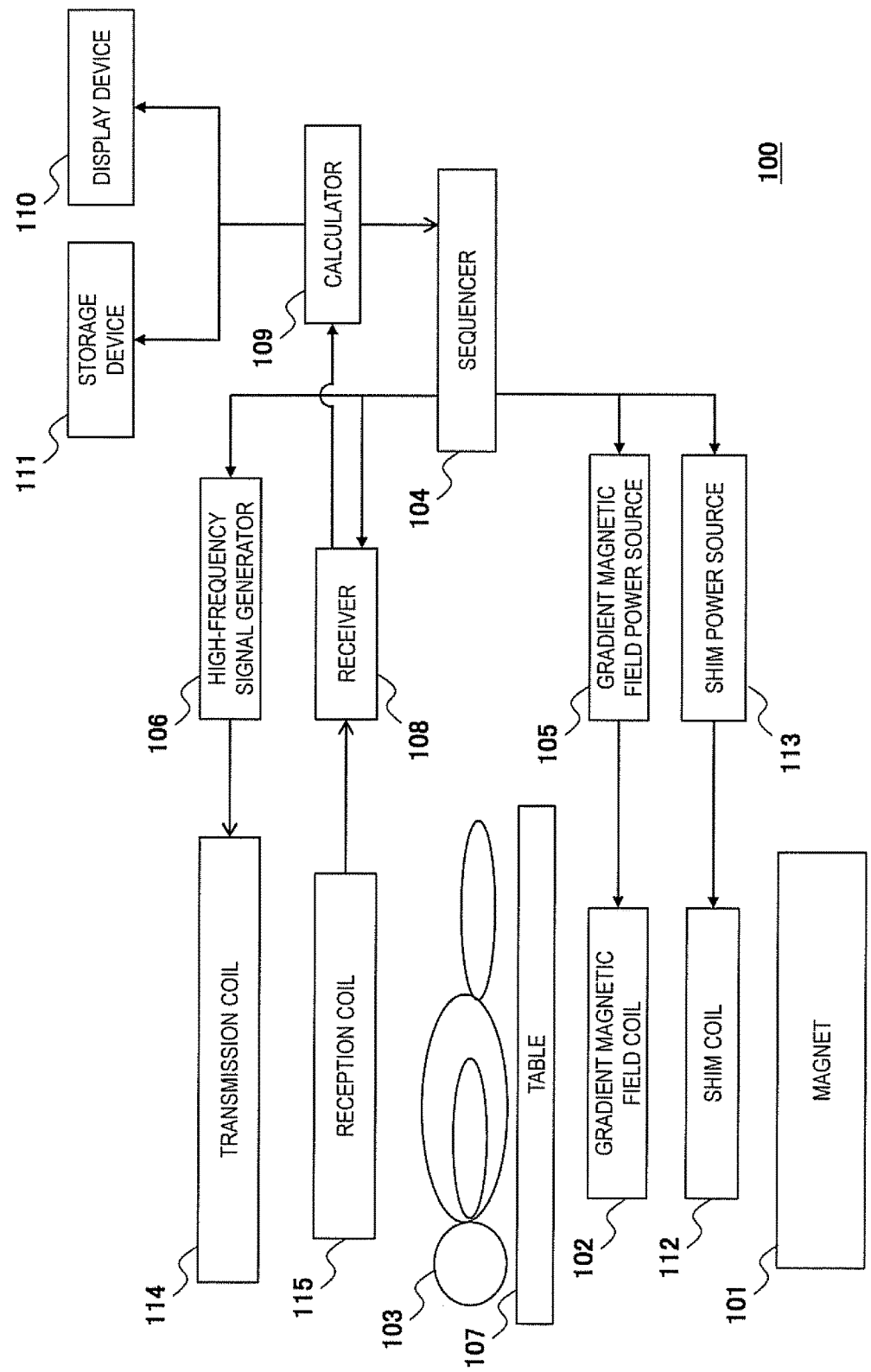
FIG. 1 is a block diagram of an MRI apparatus of the embodiments of the present invention.

First, the overall configuration of the MRI apparatus relating to the present invention will be described. FIG. 1 is a block diagram illustrating an example configuration of an MR1 apparatus 100 relating to the present invention. As illustrated in the present drawing, the MRI apparatus 100 comprises a magnet 101 that generates a static magnetic field; a gradient magnetic field coil 102 that generates a gradient magnetic field; a shim coil 112 that adjusts static magnetic field homogeneity; a sequencer 104; an RF transmission coil (transmission coil) 114 that irradiates (transmits) a high-frequency magnetic field ($B_1$); a RF reception coil (reception coil) 115 that detects (receives) nuclear magnetic resonance signals to be generated from an object 103; a table 107 on which the object 103 is placed; a gradient magnetic field power source 105; a high-frequency signal generator 106; a receiver 108; a shim power source 113; and a calculator (controller) 109 that controls each part of the MR1 apparatus 100 to realize imaging.

The gradient magnetic field coil 102 and the shim coil 112 are connected respectively to the gradient magnetic field power source 105 and the shim power source 113. Also, the transmission coil 114 and the reception coil 115 are connected respectively to the high-frequency signal generator 106 and the receiver 108.

Following an instruction from the calculator 109, the sequencer 104 transmits a command to the gradient magnetic field power source 105, the shim power source 113, and the high-frequency signal generator 106 in order to generate a gradient magnetic field and an RF respectively. The RF is irradiated (transmitted) to the object 103 through the transmission coil 114. By irradiating (transmitting) the RF, nuclear magnetic resonance signals to be generated from the object 103 are detected (received) by the reception coil 115, and then detection is performed in the receiver 108. A nuclear magnetic resonance frequency to be a reference for the detection in the receiver 108 is set by the calculator 109 via the sequencer 104. The detected signals are transmitted to the calculator 109 through an A/D conversion circuit, and signal processing such as image reconstruction is performed in the calculator. The result is displayed on the display device 110 connected to the calculator 109. The detected signals and measurement conditions are stored in a storage device 111 connected to the calculator 109 as needed.

The magnet 101, the shim coil 112, and the shim power source 113 configure a static magnetic field forming part that forms a static magnetic field space. The gradient magnetic field coil 102 and the gradient magnetic field power source 105 configure a gradient magnetic field application part that applies a gradient magnetic field in the static magnetic field space. Also, the transmission coil 114 and the high-frequency signal generator 106 configure a high-frequency magnetic field transmission unit that irradiates (transmits) an RF to the object 103. The reception coil 115 and the receiver 108 configure a signal reception part that detects (receives) nuclear magnetic resonance signals to be generated from the object 103.

<<Multi-channel Transmission Coil>>

The transmission coil 114 is a multi-channel transmission coil that is provided with a plurality of channels transmitting an RF independently. FIG. 2(A) shows an example of the transmission coil 114. The example shows a case where the transmission coil 114 is a four-channel (4-ch) coil having four channels (114-1 (channel 1), 114-2 (channel 2), 114-3 (channel 3), and 114-4 (channel 4) that are arranged counterclockwise from the upper left). However, the present invention is not limited to the four channels, and the arbitrary number of channels (approximately 2 to 256) can be applied. The amplitude and the phase of an RF to be transmitted from each of the channels (114-1, 114-2, 114-3, and 114-4) are set by the calculator 109 respectively and independently. According to the control from the calculator 109, the high-frequency signal generator 106 independently transmits an RF signal to each of the channels through electricity supply points (117-1, 117-2, 117-3, and 117-4) with which each of the channels (114-1, 114-2, 114-3, and 114-4) is provided. It is noted that 116 is an RF shield in the present drawing.

<<RF Irradiation Method>>

Next, an RF irradiation method using the transmission coil 114 will be described. Here, a case of imaging an abdominal region of the object 103 is taken as an example and described. When imaging the abdominal region, an imaging region 201 of the object 103 is set as illustrated in FIG. 2(B).

FIG. 2(C) shows an electromagnetic field simulation result of a rotating magnetic field $B_1$ ($B_1$ distribution) 202 to be generated in a phantom 200 when an RF is irradiated from the transmission coil 114 to the phantom 200 that represents the abdominal region of the object 103.

In this simulation, $B_1$ strength inside the imaging region 201 is made dimensionless so that the maximum $B_1$ strength in the phantom 200 is 1. The measurements in the x-, y-, and z-axis directions of the phantom 200 are set to 300 mm, 200 mm, and 900 mm respectively. This is a simplified shape, assuming an abdominal cross section of the biological body. Also, the physical property of the phantom 200 has a conductivity of 0.6 S/m and a specific inductive capacity of 80. This is determined by assuming a water phantom whose physical property is close to the biological body. The frequency of an RF to be irradiated is set to 128 MHz, assuming a 3T MRI apparatus.

Also, voltages of the sine waveforms shown in the following formula (1) is supplied to the electricity supply points (117-1, 117-2, 117-3, and 117-4) of the respective channels (114-1, 114-2, 114-3, and 114-4).

$$\left.\begin{array}{l} B\_ch1 = A1\sin(\omega t + \phi 1) \\ B\_ch2 = A2\sin(\omega t + \phi 2) \\ B\_ch3 = A3\sin(\omega t + \phi 3) \\ B\_ch4 = A4\sin(\omega t + \phi 4) \end{array}\right\} \quad (1)$$

A1 and φ1 respectively show an amplitude and a phase of a sine waveform voltage to be supplied to the electricity supply point 117-1 of the channel 114-1, A2 and φ2 respectively show the same amplitude and the same phase to be supplied to the electricity supply point 117-2 of the channel 114-2, A3 and φ3 respectively show the same amplitude and the same phase to be supplied to the electricity supply point 117-3 of the channel 114-3, and A4 and φ4 respectively show the same amplitude and the same phase to be supplied to the electricity supply point 117-4 of the channel 114-4. Also, in the $B_1$ distribution 202 illustrated in FIG. 2(C), A1, A2, A3, and A4 are set to 1, and the phases are set to φ1=0, φ2=π/2, φ3=π, and φ4=π/2. This is an RF irradiation method referred to as QD (Quadrature Drive) and is a standard RF irradiation method.

When RF waveforms are transmitted from the respective channels (114-1, 114-2, 114-3, and 114-4) at the same amplitude and in a different phase by π/2 similarly to the QD irradiation, $B_1$ strength varies greatly and becomes inhomogeneous in the imaging region 201 of a phantom as illustrated in FIG. 2(C). This is an example of $B_1$ inhomogeneity that is a problem in a high magnetic field MRI apparatus.

<<Controller Functions>>

Figure 3:
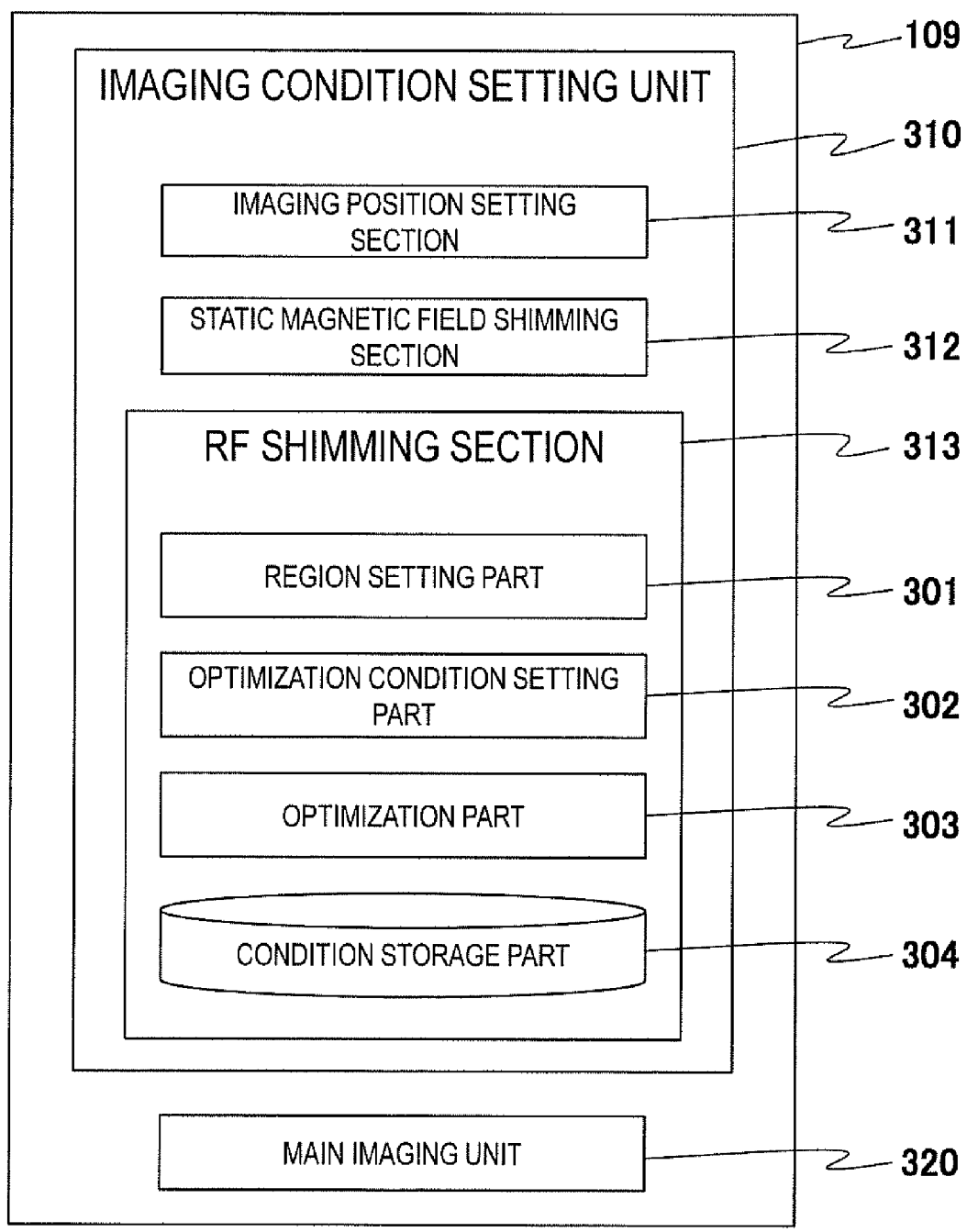
FIG. 3 is a functional block diagram of a calculator of an embodiment of the present invention.

The calculator (controller) 109 relating to the present invention controls each part relating to imaging of the MRI apparatus 100 so as to acquire high-quality images by homogenizing a $B_1$ distribution and reducing a SAR. In order to achieve this, the calculator 109 comprises an imaging condition setting unit 310 that sets imaging conditions and a main imaging unit 320 that performs main imaging according to the imaging conditions set by the imaging condition setting unit 310 as illustrated in FIG. 3. Also, the imaging condition setting unit 310 comprises an imaging position setting section 311, a static magnetic field shimming section 312, and an RF shimming section 313.

The imaging position setting section 311 sets an imaging position (imaging cross section). The imaging cross section is set using a positioning image acquired in a scout scan or the like executed before main imaging. For example, an operator designates a position on the positioning image displayed on the display device 110 to set the designated position as the imaging cross section. A predetermined position for each site as an imaging cross section may be automatically set using characteristics or the like on the positioning image. It is noted that an object 103 region on the imaging cross section is referred to as an imaging region.

The static magnetic field shimming section 312 measures a static magnetic field distribution and performs adjustment so as to homogenize the static magnetic field as possible. The adjustment is performed by operating the shim coil 112 through the shim power source 113. It is noted that the static magnetic field shimming section 312, the shim coil 112, and the static magnetic field shimming section 312 are not required in a case where static magnetic field homogeneity adjustment is unnecessary.

The RF shimming section 313 performs an RF shimming process that determines at least one of an amplitude and a phase of an RF to be transmitted from the respective channels (114-1, 114-2, 114-3, and 114-4) of the transmission coil 114. The RF shimming section 313 relating to the present invention determines at least one of an amplitude and a phase of an RF to be transmitted from the respective channels so as to acquire high-quality images by homogenizing a $B_1$ distribution and reducing a SAR as described above. Hereinafter, at least one of the amplitude and the phase of the RF to be transmitted to the respective channels of the transmission coil 114, for which the RF shimming section 313 of the present embodiment performs determination, is referred to as a high frequency magnetic field condition.

<<Detailed Functions of RF Shimming Section>>

Next, the details of the RF shimming section 313 relating to the present invention will be described. In order to realize the above RF shimming process, the RF shimming section 313 relating to the present invention 313 comprises a region setting part 301, an optimization condition setting part 302, an optimization part 303, and a condition storage part 304.

The RF shimming section 313 adjusts amplitudes (A1, A2, A3, and A4) and phases (φ1, φ2, φ3, and φ4) of RFs to be transmitted to the respective channels (114-1, 114-2, 114-3, and 114-4) so as to reduce $B_1$ inhomogeneity in a region to be particularly diagnosed (diagnostic region) in the imaging region 201, and an optimal one is set as a high frequency magnetic field condition. At this time, the RF shimming section 313 of the present embodiment adjusts these parameter values so as to further reduce a SAR.

Additionally, the RF shimming section 313 first identifies a suppression region and a diagnostic region whose image can be acquired with high image quality in an imaging region as needed. The suppression region is different from the diagnostic region, and, for example, can be set as a region where artifacts are generated in the diagnostic region or a region where a local SAR increases. Then, while $B_1$ inhomogeneity in the diagnostic region is being increased, a high frequency magnetic field condition is determined so as to reduce $B_1$ in the suppression region.

Figure 4:
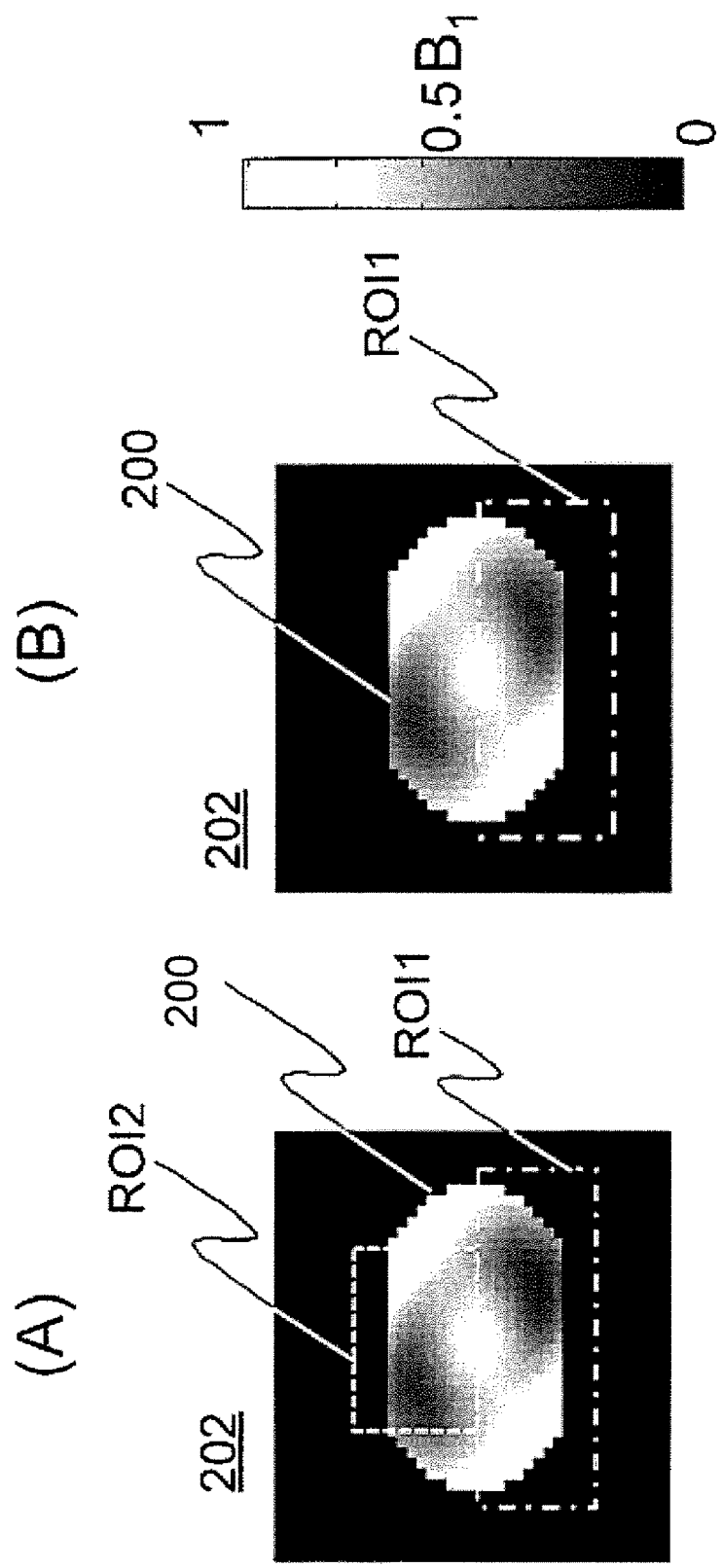
FIG. 4(A) is an explanatory view illustrating a setting example of first and second regions of an embodiment of the present invention.
FIG. 4(B) is an explanatory view illustrating a setting example of the first region of an embodiment of the present invention.

The region setting part 301 sets a diagnostic region and a suppression region as a first region ROI 1 and a second region ROI 2 respectively. The setting is performed by receiving a region designated on a positioning image or based on a result of $B_1$ distribution measurement that is performed after setting a high frequency magnetic field condition to an initial value by an operator. That is, the region setting part 301 sets the first region ROI 1 and the second region ROI 2 according to the instruction from the operator. FIG. 4(A) shows a setting example of the first region ROI 1 and the second region ROI 2 in a case where the abdomen is designated as an imaging site.

Alternatively, the first region ROI 1 that is a diagnostic region and the second region ROI 2 that is a suppression region may be configured so as to be automatically set according to an imaging site and an imaging purpose. In this case, the MRI apparatus 100 further comprises a region storage unit that stores the first region ROI 1 and the second region ROI 2 according to the site and the imaging purpose, and the region setting part 301 extracts the first region ROI 1 and the second region ROI 2 stored according to the imaging site or the imaging purpose set in the imaging conditions from the region storage unit after the site and the imaging purpose are set as imaging conditions in order to set the regions. The region storage unit is previously provided in the storage device 111.

It is noted that the entire object 103 region may be set as a diagnostic region (a first region ROI 1) without setting a suppression region (a second region ROI 2).

The optimization part 303 determines at least one of amplitudes (A1, A2, A3, and A4) and phases (φ1, φ2, φ3, and φ4) of RFs to be transmitted to the respective channels (114-1, 114-2, 114-3, and 114-4) as a high frequency magnetic field condition so as to optimize a $B_1$ distribution in a first region ROI 1. In the present invention, as described above, the high frequency magnetic field condition is determined so that inhomogeneity of the $B_1$ distribution in the first region ROI 1 is equal to or more than a predetermined value and so as to reduce a SAR. In the present invention, the high frequency magnetic field condition is acquired as a solution that minimizes a predetermined objective function under a predetermined restriction condition.

The solution is calculated using solution methods method of the optimization problem such as a steepest descent method, a gradient method, a Newton method, a least square method, a conjugate gradient method, a linear programming method, and a non-linear programming method.

Also, a solution minimizing an objective function may be evaluated by comprehensively changing values of an amplitude and a phase. For example, an objective function value is calculated by changing the values of the amplitude and the phase respectively by 1 dB and 5 degrees in order to evaluate an amplitude and a phase when the objective function value is minimized. However, in a case where it takes an enormous calculation time to comprehensively change the amplitude and the phase, for example, an amplitude and a phase that acquires a minimum value of the objective function are evaluated in a state where change amounts of the amplitude and the phase are increased at the beginning, and then the amplitude and the phase may be evaluated in a state where the change amounts are reduced in the vicinity of values of the amplitude and the phase.

Initial values of an amplitude and a phase for these solution methods are previously stored in the storage device 111. Also, in a case where an optimal amplitude and an optimal phase are previously predicted to some extent, the predicted value is set as an initial value, and then an amplitude and a phase may be comprehensively changed only for values in the vicinity of the initial value.

Here, the optimization part 303 may acquire a $B_1$ value in an imaging region by performing $B_1$ distribution measurement that measures a $B_1$ distribution in the imaging region each time the high frequency magnetic field condition is changed. Also, the high frequency magnetic field condition may be determined by changing only one of an amplitude and a phase.

The condition storage part 304 stores a pair of a restriction condition that the optimization part 303 uses for calculating the high frequency magnetic field condition and an objective function (optimization condition). The optimization condition setting part 302 sets optimization conditions that the optimization part 303 uses for calculating the high frequency magnetic field condition. The optimization part 303 uses the set optimization conditions to calculate the high frequency magnetic field condition.

<<Process Flow of RF Shimming>>

Figure 5:
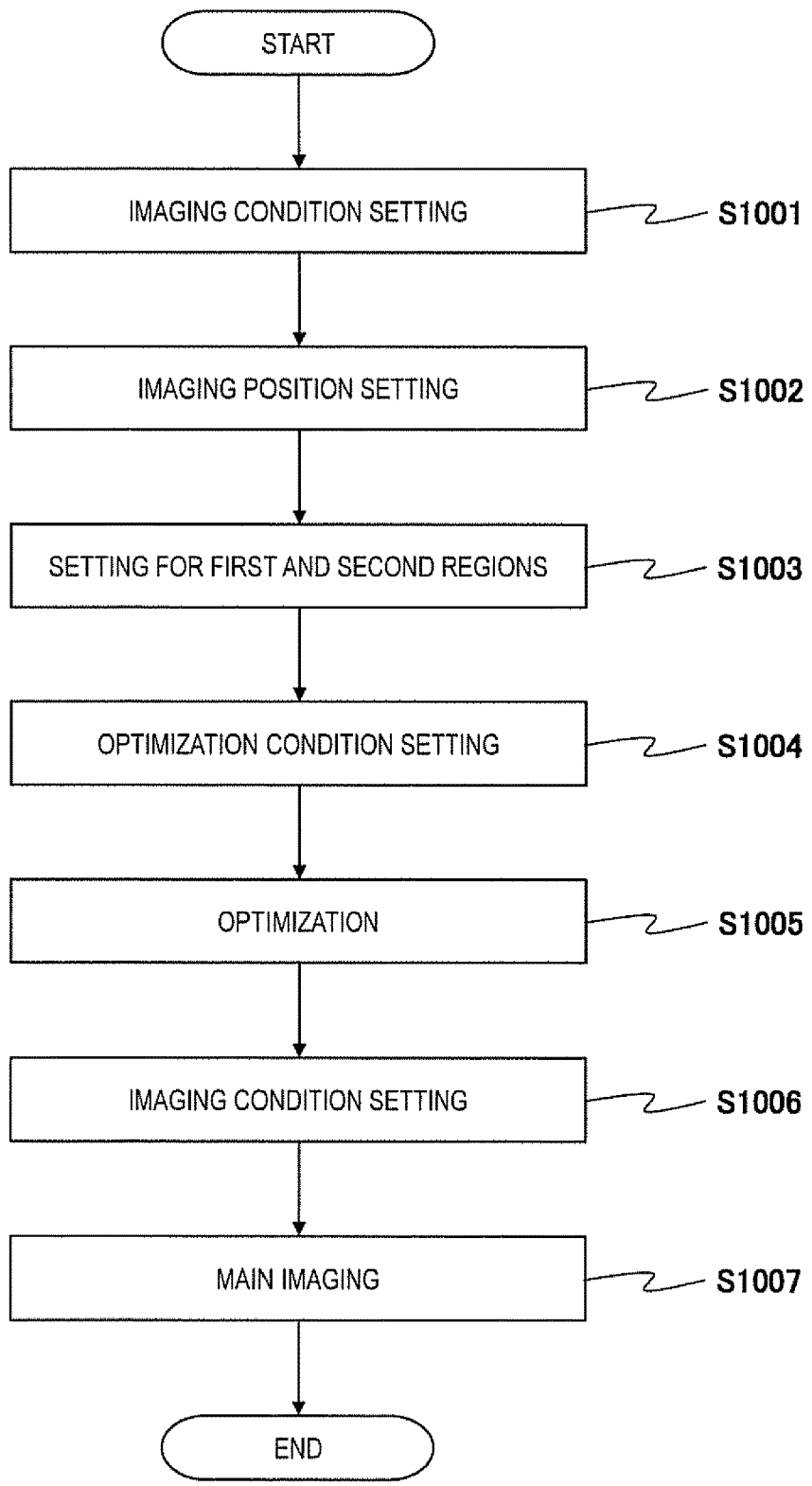
FIG. 5 is a flow chart of imaging processing of an embodiment of the present invention.

Next, FIG. 5 shows an example flow of imaging processes including an RF shimming process that relates to the present invention and in which the respective functions of the above RF shimming section 313 cooperate with each other. The present imaging process starts with an instruction from an operator.

Next, the imaging condition setting unit 310 receives input of imaging conditions including imaging parameters, an imaging site, an imaging purpose, and the like from an operator and sets the conditions (Step S1001). Next, the imaging position setting section 311 performs a scout scan to set an imaging position (Step S1002). Then, the region setting part 301 sets the first region ROI 1 and the second region ROI 2 (Step S1003). It is noted that the present process of Step S1003 is omitted when the second region ROI 2 is not set as described above.

Next, the optimization condition setting part 302 sets an optimization condition comprising a pair of an objective function and a restriction condition (Step S1004). The optimization part 303 performs optimization to evaluate a solution that minimizes an objective function under the restriction condition set by the optimization condition setting part 302 (Step S1005). Then, the imaging condition setting unit 310 sets imaging conditions together with the other imaging parameters as an amplitude and a phase (high-frequency magnetic field conditions) of an RF to be transmitted to each channel that uses the solution evaluated by the optimization part 303 for imaging (Step S1006).

Then, the main imaging unit 320 performs main imaging according to imaging conditions including the high frequency magnetic field condition set by the imaging condition setting unit 310 (Step S1007). Specifically, the main imaging unit 320 generates a high frequency (RF) for each of the channels to the high-frequency signal generator 106 based on the high frequency magnetic field condition and supplies the high frequency to each channel of the transmission coil 114 in order to execute main imaging.

A CPU provided with the calculator 109 loads a previously stored program in the storage device 111 in a memory and executes the program in order to realize each function to be realized by the calculator 109. It is noted that the condition storage part 304 may be constructed on the storage device 111.

<<Index to be Used in Present Invention>>

Next, an example of an index showing homogeneity of a $B_1$ distribution to be used in the present invention will be described. As an example of the index showing homogeneity of the $B_1$ distribution in the imaging region 201, a $B_1$ distribution homogeneity index $U_{SD}$ shown in the following formula (2) can be used. The $B_1$ distribution homogeneity index $U_{SD}$ is a value in which a standard deviation of a $B_1$ value ($\sigma(B_1)$) was divided by a $B_1$ average value ($m(B_1)$). The smaller the $B_1$ distribution homogeneity index $U_{SD}$, the $B_1$ distribution in a target region becomes homogeneous.

$$U_{SD} = \frac{\sigma(B_1)}{m(B_1)} \quad (2)$$

Furthermore, an example of an objective function relating to the present invention will be described. The objective function is represented in the formula (3).

$$f = w \times \frac{\sum_{i=1}^{ch} w_{amp}(i) \times \text{amp}(i)^k}{ch} + (1-w) \frac{U_{sd}(shim)}{U_{sd}(QD)} \quad (3)$$

The following represents each member of the formula (3). That is, the first term relates to SAR reduction and evaluates how small an RF amplitude becomes compared to a case of QD irradiation. Therefore, the first term is formed by performing weighted addition for an exponential of the RF amplitude of each channel in order to reflect a SAR difference between each channel. On the other hand, the second term relates to improvement of the $B_1$ distribution homogeneity and evaluates to what degree the $B_1$ distribution homogeneity is improved compared to a case of QD irradiation. That is, an objective function relating to the present invention that is represented in the formula (3) is a linear combination in which the first term showing the SAR reduction and the second term showing the improvement of the $B_1$ distribution homogeneity are weighted with a weight (w).

More specifically, in the formula (3), w(0<=w<=1) represents a distribution weight relating to distribution of the SAR reduction and the improvement of the $B_1$ distribution homogeneity. $w_{amp}$ represents a weight relating to adjusting an amplitude for each of the channels of a transmission coil and is a value to be set for each of the channels, and $w_{amp}(i)$ is a value of an amplitude weight of an i-th channel and is 0 or a positive number (approximately 0<=$w_{amp}(i)$<=10). An amplitude exponent k represents the k-th power of the amplitude and is 0 or a positive number (approximately 0<=k<=4). ch represents the number of channels of an irradiation coil, and, for example, ch=4 is shown in a case of 4-channel configuration. Also, $U_{sd}$(shim) is a value in which $U_{sd}$ in the formula (3) was evaluated using an RF shim parameter after RF shimming, and $U_{sd}$ (QD) is a value in which $U_{sd}$ in the formula (3) was evaluated using an RF shim parameter after QD irradiation.

As described above, as a distribution weight w becomes greater, contribution of the first term becomes greater, which further reduces a SAR. On the other hand, as a distribution weight w becomes less, contribution of the second term becomes greater, which improves $B_1$ distribution homogeneity. Although 2 is normally used for k, a value other than 2 may be used. Considering that a value of approximately 1 is normally used for an amplitude, as k becomes greater, the contribution of the first term becomes greater, which reduces the amplitude as well as the SAR.

Hereinafter, a distribution weight (w), a weight ($w_{amp}$) of each of the channels, and an exponent (k) are altogether referred to as objective function parameters.

Considering the above altogether, in an example of an objective function using the objective function parameters relating to the present invention:

the objective function parameters include a distribution weight (w), a weight ($w_{amp}$) of each of the channels, and an exponent (k);

the objective function is a linear combination in which a term showing SAR reduction and a term showing improvement of $B_1$ distribution homogeneity are weighted with a distribution weight (w); and the term showing SAR reduction is formed by performing weighted addition for an exponential (the k-th power) of an RF amplitude for each channel with a weight ($w_{amp}$), therefore, an RF shimming section determines a high frequency magnetic field condition as a solution that optimizes the set objective function.

<<Basic Configuration of Present Invention>>

Generally, in most cases of examination with an MRI apparatus, an object is shifted from the magnetic field center before disposition. Hence, in a case of a multi-channel transmission coil, a SAR becomes higher in a channel disposed in a position relatively closer to the object than a channel disposed in a position relatively farther from the object.

Therefore, in the present invention, objective function parameter values for setting an objective function such as the above formula (3) are determined according to contribution to an SAR. A weight ($w_{amp}$) of each channel that is one of the objective function parameters is greater in a channel whose contribution to a SAR is relatively large than a channel whose contribution to a SAR is relatively small. For example, the weight ($w_{amp}$) of a channel disposed in a position relatively closer to an object is set greater than the weight ($w_{amp}$) of a channel disposed in a position relatively farther from the object. Hence, entire SAR reduction of a transmission coil and improvement of $B_1$ distribution homogeneity coexist with each other.

Hereinafter, in each embodiment relating to the present invention, setting the above objective function parameter values will be described to set an objective function according to contribution to a SAR of each channel. In each embodiment to be described below, described is a case of setting the entire of an object 103 region as a diagnostic region (the first region ROI 1) without setting a suppression region (the second region ROI 2), but a case of setting the suppression region (the second region ROI 2) can also be implemented similarly.

<<First Embodiment>>

A first embodiment of the present invention will be described. The first embodiment is characterized by previously setting objective function parameter values for an MRI apparatus and using these values.

In most cases in examination with an MRI apparatus, an object is disposed on a side lower than the magnetic field center. Because of this, contribution to a SAR is relatively greater in channels disposed on the lower side relatively closer to an object than channels disposed on the upper side relatively farther from the object when imaging is performed using a multi-channel transmission coil. Therefore, in the first embodiment, weights ($w_{amp}$) of the lower channels are set relatively greater than weights ($w_{amp}$) of the upper channels.

Although configuration of each function of the RF shimming section 313 in the first embodiment is similar to the configuration illustrated in the above FIG. 3, the processes of the following functional parts vary.

Objective function parameter values are previously stored in the condition storage part 304, and the optimization condition setting part 302 reads those values to set an objective function.

Also, although a process flow of the RF shimming section 313 is similar to the process flow illustrated in the above FIG. 5, a process of the following step varies.

When the optimization condition setting part 302 extracts optimization conditions from the condition storage part 304 in Step S1004, objective function parameter values are also read to set an objective function.

Because the other processes are similar to the process flow of FIG. 5, the description is omitted.

Figure 6:
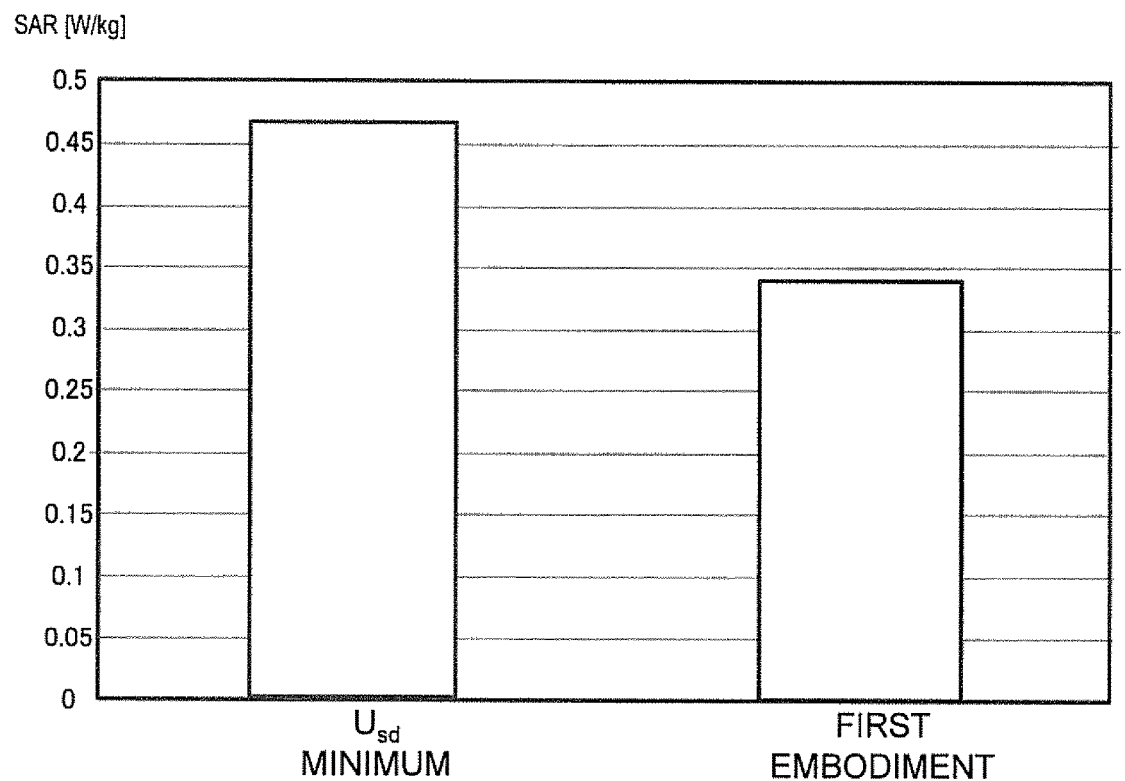
FIG. 6 is a specific example of a first embodiment, in which imaging is performed using a four-channel transmission coil as illustrated in FIG. 2(A), and shows a measurement result of a whole-body SAR.

Next, cases of imaging using the four-channel transmission coil as illustrated in FIG. 2(A) are illustrated in FIGS. 6 and 7 as a specific example of the first embodiment. The four-channel transmission coil illustrated in FIG. 2(A) has a configuration where the channels 1 and 4 are disposed on the upper side and the channels 2 and 3 are disposed on the lower side. Therefore, in the cases of FIGS. 6 and 7, the objective function parameter values are set as follows:

Distribution weight: w=0.5
Amplitude exponent: k=2
Upper channel weight: $w_{amp}(i)$=0.4 i=1, 4
Lower channel weight: $w_{amp}(i)$=1.6 i=2, 3

FIG. 6 shows measurement results of a whole-body SAR including a measurement result for which an amplitude and a phase of each channel determined by the first embodiment and a measurement result for which an amplitude and a phase of each channel determined by a method for minimizing a conventional $U_{sd}$. The vertical axis indicates a whole-body SAR value. Although the whole-body SAR was 0.3 [W/kg] in a conventional method, the whole-body SAR is 0.23 [W/kg] in the first embodiment, which can achieve approximately 25% reduction.

Also, FIG. 7 shows measurement results of a $B_1$ map of an entire FOV including a measurement result (FIG. 7(A)) for which an amplitude and a phase of each channel determined by the first embodiment and a measurement result (FIG. 7(B)) for which an amplitude and a phase of each channel determined by a method for minimizing a conventional $U_{sd}$. Although homogeneity of a $B_1$ distribution of the entire FOV was $U_{sd}$=0.116 in a conventional method, the homogeneity is 0.119 in the first embodiment, which can minimize deterioration to only approximately 3%.

That is, the examples of the first embodiments illustrated in FIGS. 6 and 7 show that a SAR can be reduced while maintaining homogeneity of the $B_1$ distribution (without being deteriorated substantially).

As describe above, the first embodiment sets an objective function using objective function parameter values that were preset by previously assuming a position in which an object is disposed, which can easily achieve SAR reduction as well as maintenance and improvement of $B_1$ distribution homogeneity without detecting the position in which an object is disposed.

<<Second Embodiment>>

A second embodiment of the present invention will be described. The second embodiment is characterized by using different objective function parameter values according to an imaging site (and/or an imaging purpose) of an object.

For example, in a case of imaging the breast, an object is usually disposed in a magnetic field space so that the breast of the object is located in the magnetic field center or the vicinity thereof. In this case, since the object gets close to the upper channels, SAR contribution of the upper channels is relatively increased compared with the lower channels. Therefore, in a case of imaging the breast, homogeneity can be improved while the SAR is reduced by setting $w_{amp}$ of the upper channels greater than $w_{amp}$ of the lower channels.

Also, in a case of imaging the shoulders and the arms, because an object is disposed in a magnetic field space so that a shoulder and an arm on a side to be imaged are located in the magnetic field center or the vicinity thereof, the object is to be disposed off-center in the horizontal direction in the magnetic field space. In this case, $B_1$ distribution homogeneity can be improved while the SAR is reduced by setting weights ($w_{amp}$) of channels on a side closer to the obejct greater than weights ($w_{amp}$) of channels on a side farther from the obejct.

Therefore, in the second embodiment, objective function parameter values are stored in advance for each of the imaging sites (and/or imaging purposes) of an object. Then, the settings for the imaging site (and/or the imaging purpose) are received from an operator, an objective function parameter value corresponding to the imaging site (and/or the imaging purpose) set by the operator is selected from the objective function parameter values for each of the imaging sites (and/or imaging purposes) stored in advance, and then the selected value is used for setting an objective function.

Although configuration of each function of the RF shimming section 313 for realizing the second embodiment is similar to the configuration illustrated in the above FIG. 3, the processes of the following functional parts vary.

The imaging condition setting unit 310 receives input of imaging conditions including an imaging site (and/or an imaging purpose) from an object to set the input imaging site (and/or imaging purpose), The condition storage part 304 previously stores objective function parameter values are stored for each of the imaging sites (and/or imaging purposes).

The optimization condition setting part 302 extracts an objective function parameter value corresponding to an imaging site (and/or an imaging purpose) set by the imaging condition setting unit 310 from among the objective function parameter values for each of the imaging sites (and/or imaging purposes) stored in the condition storage part 304 in order to set an objective function using the extracted value.

Also, although the process flow of the RF shimming section 313 is similar to that illustrated in the above FIG. 5, the processes of the following steps vary.

In Step S1001, the imaging condition setting unit 310 receives input of imaging conditions including an imaging site (and/or an imaging purpose) and sets the imaging conditions.

In Step S1004, the optimization condition setting part 302 extracts an objective function parameter value corresponding to an imaging site (and/or an imaging purpose) set in Step S1001 from among the objective function parameter values for each of the imaging sites (and/or imaging purposes) stored in the condition storage part 304 in order to set an objective function using the extracted value.

The other processes are similar to the process flow of FIG. 5, and the description is omitted.

FIG. 8 shows an example of objective function parameter values for each of the imaging sites. A database in which the combinations of the imaging sites and the objective function parameter values are set for each of the imaging sites is prepared in advance to be stored in the condition storage part 304.

Next, as a specific example of the second embodiment, a case of imaging the shoulders and the arms using the four-channel transmission coil illustrated in FIG. 2.

In a case of imaging the right shoulder or the right arm of an object, the right channels 3 and 4 are relatively closer to the left shoulder and the left arm of the object, and the left channels 1 and 2 are relatively farther from the right shoulder or the right arm of the object. Therefore, a weight ($w_{amp}$) of the right channels 3 and 4 is set greater than a weight ($w_{amp}$) of the left channels 1 and 2. For example, the objective function parameter values can be set as follows:

Distribution weight: w=0.5
Amplitude exponent: k=2
Left channel weight: $w_{amp}(i)$=0.4 i=1, 2
Right channel weight: $w_{amp}(i)$=1.6 i=3, 4

Furthermore, in a case where an object is disposed with the position shifted in the vertical direction, objective function parameter values can be set in combination with the above first embodiment. For example, in a case where the object is disposed with the position shifted to the lower side, weights are varied between the upper and lower channels so that a weight ($w_{amp}$) of the lower channels is greater than a weight ($w_{amp}$) of the upper channels. For example, the objective function parameter values can be set as follows:

Upper left channel (i=1) weight: $w_{amp}(1)$=0.4
Lower left channel (i=2) weight: $w_{amp}(2)$=0.5
Lower right channel (i=3) weight: $w_{amp}(3)$=1.7
Upper right channel (i=4) weight: $w_{amp}(4)$=1.6

Contrarily, in a case of setting the left shoulder or the left arm of an object as an imaging target, a weight ($w_{amp}$) of the left channels 1 and 2 is set greater than a weight ($w_{amp}$) of the right channels 3 and 4. Furthermore, in a case where the object is disposed with the position shifted in the vertical direction, those weights may be changed even between the upper and lower channels.

As described above, the second embodiment previously stores objective function parameter values for each of the imaging sites (and/or imaging purposes), selects an objective function parameter value corresponding to the imaging site (and/or the imaging purpose) set by the operator from among the previously stored objective function parameter values for each of the imaging sites (and/or imaging purposes) according to the settings for the imaging site (and/or the imaging purpose) from an operator, and uses the selected value for setting an objective function. That is, different objective function parameter values are used according to the imaging site of the object (and/or the imaging purpose). Hence, SAR reduction as well as maintenance and improvement of $B_1$ distribution homogeneity can be achieved more accurately and easily according to an imaging site (and/or an imaging purpose) without detecting a position in which an object is disposed.

<<Third Embodiment>>

A third embodiment of the present invention will be described. The third embodiment is characterized by that an operator sets objective function parameter values.

When imaging conditions are set, a GUI (Graphical User Interface) for setting and inputting objective function parameters (w, k, $w_{amp}$) for each of the channels is displayed so that an operator inputs and sets the objective function parameter values. Alternatively, a plurality of combinations of parameter values prepared in advance, and it may be configured so that the operator selects a desired combination from among the combinations. Then, an objective function is set based on the input objective function parameter values in order to evaluate a high-frequency magnetic field condition for optimizing the objective function set under a restriction condition.

Figure 9:
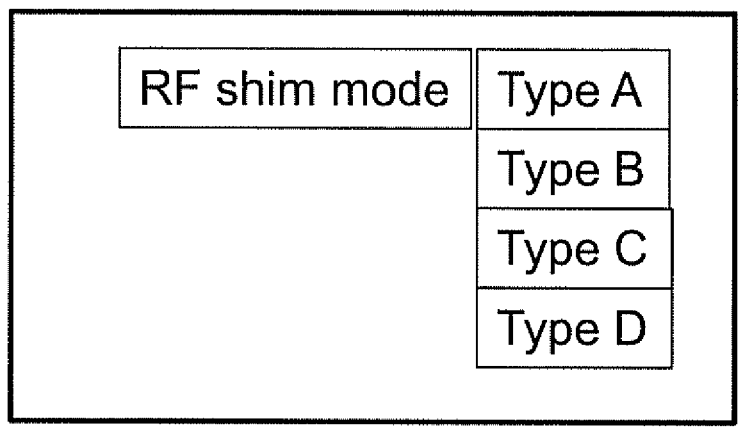
FIG. 9 is a specific example of a third embodiment and shows an example of a GUI for setting and inputting the objective function parameter values.

FIG. 9 shows an example of a GUI for setting and inputting objective function parameter values. The example shown in FIG. 9 illustrates a GUI that displays a plurality of combinations of parameter values prepared in advance so that an operator selects a desired combination from among the combinations. In FIG. 9, "RF Shim Mode" is the setting item for the objective function parameter values, the following options are displayed by clicking this, and then an objective function parameter value is set by selecting an arbitrary one therefrom. The options mean respectively as follows:

Type A: QD irradiation
Type B: RF shim parameter calculation by an objective function of the present invention
Type C: RF shim parameter calculation by setting $U_{sd}$ as an objective function
Type D: RF shim parameter calculation by setting $U_{sd}$ as an objective function using a $B_1$ map of a partial region.

Although configuration of each function of the RF shimming section 313 for realizing the third embodiment is similar to the configuration illustrated in the above FIG. 3, the processes of the following functional parts vary.

The optimization condition setting part 302 displays a GUI for setting and inputting objective function parameter values on the display device 110 and receives input of objective function parameter values by an operator in order to set an objective function based on the input objective function parameter values.

Also, although the process flow of the RF shimming section 313 is similar to the process flow illustrated in the above FIG. 5, the processes in the following steps vary.

In Step S1001, the imaging condition setting unit 310 displays a GUI for setting and inputting objective function parameter values on the display device 110 and receives input of objective function parameter values by an operator in order to set the input value as an objective function parameter value.

In Step S1004, the optimization condition setting part 302 sets an objective function based on the objective function parameter value set in Step S1001.

The other processes are similar to the process flow of FIG. 5, and the description is omitted.

As described above, in the third embodiment, setting objective function parameter values by an operator is received in order to set an objective function based on the input objective function parameter values. Hence, an operator can freely select a channel that reduces a SAR.

<<Fourth Embodiment>>

A fourth embodiment of the present invention will be described. The fourth embodiment is characterized by that distances between an object and each channel are determined based on a positioning image in order to set objective function parameter values based on the determined distances.

In a general MRI examination, a positioning image of three orthogonal cross sections or the like is acquired before main imaging in order to determine an imaging position or an imaging region of an object. Then, a position in which the object is disposed in a magnetic field space can be determined using the positioning image. On the other hand, positions in which the respective channels of the transmission coil are arranged in the magnetic field space are previously known from data provided when the MRI apparatus was designed, and the values can be stored. Therefore, distances between the object and each of the channels can be evaluated based on the object disposition position determined using the positioning image and the design data for the disposition positions of each of the channels. Based on the evaluated distances, to which channel the object is relatively closer or from which channel the object is relatively farther can be determined. Then, a weight ($w_{amp}$) of a channel in a position relatively closer to the object is set greater than a weight ($w_{amp}$) of a channel in a position relatively farther from the object. Alternatively, the weight ($w_{amp}$) of the channel may be determined based on a distance (d) between the object and each of the channels as shown in the following formula (4).

$$w_{amp} = w_{max} \cdot \exp(-\lambda \cdot d) \qquad (4)$$

Here, $w_{max}$ is a maximum weight value, and $\lambda$ is a predetermined distance attenuation coefficient.

Although configuration of each function of the RF shimming section 313 for realizing the fourth embodiment is similar to the configuration illustrated in the above FIG. 3, the processes of the following functional parts vary.

Disposition positions of the respective channels of the transmission coil in a magnetic field space are acquired from the design data of an MRI apparatus. The condition storage part 304 stores the disposition positions.

The imaging position setting section 311 acquires a positioning image by performing a scout scan or the like in order to determine a disposition position of an object in a magnetic field space based on the acquired positioning image.

The optimization condition setting part 302 evaluates distances between an object and each channel based on the disposition position of the object in the magnetic field space evaluated by the imaging position setting section 311 and the disposition position of each channel in the magnetic field space read from the condition storage part 304. Based on the distances, a weight ($w_{amp}$) of a channel in a position relatively closer to the object is set greater than a weight ($w_{amp}$) of a channel in a position relatively farther from the object. Alternatively, weights ($w_{amp}$) of the respective channels are determined using the above formula (4).

Also, although the process flow of the RF shimming section 313 is similar to the process flow illustrated in the above FIG. 5, the processes in the following steps vary.

In Step S1002, the imaging position setting section 311 acquires a positioning image by performing a scout scan or the like. Then, as described above, distances between an object and each channel are evaluated based on the acquired positioning image.

In Step S1004, the optimization condition setting part 302 sets a weight ($w_{amp}$) of a channel 1 in a position relatively closer to an object greater than a weight ($w_{amp}$) of a channel in a position relatively farther from the object based on the distances between the object and each channel that were evaluated in Step S1002. Alternatively, based on the distances between the object and each channel, a weight ($w_{amp}$) of the channel as shown in the above formula (4) is determined. Then, an objective function is set based on the determined weight ($w_{amp}$) of each channel.

The other processes are similar to the process flow of FIG. 5, and the description is omitted.

Figure 10:
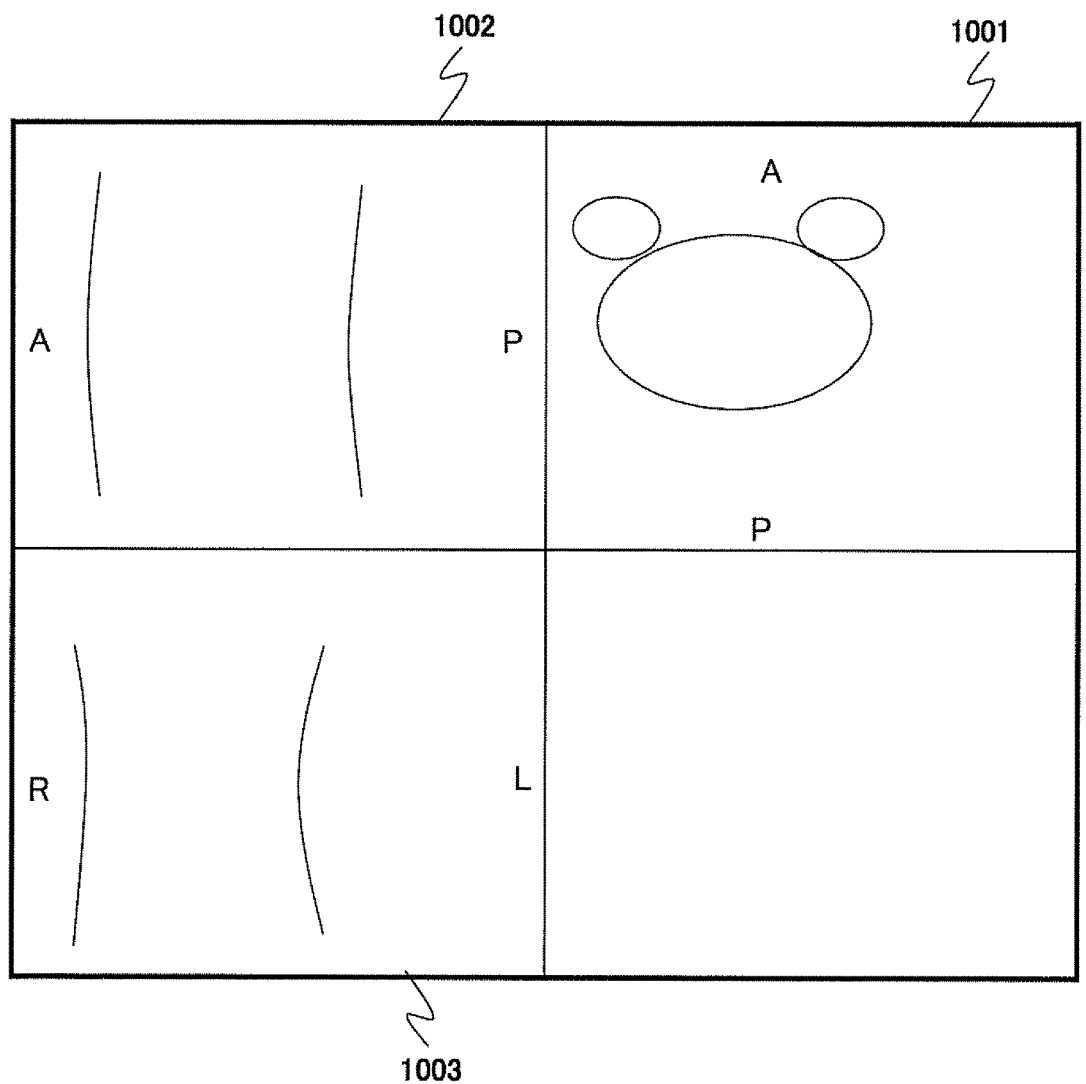
FIG. 10 is a specific example of a fourth embodiment and shows an example of an orthogonal three-cross-section image that is a positioning image of an object imaged with the arms placed on the abdomen using the transmission coil with a plurality of channels that is illustrated in FIG. 2.

FIG. 10 shows an example of an orthogonal three-cross-section image that is a positioning image of an object imaged with the arms placed on the abdomen using the transmission coil with a plurality of channels that is illustrated in FIG. 2. 1001 is an axial image, 1002 is a sagittal image, and 1003 is a coronal image. From these cross-sectional images, it can be understood that the object is disposed with the position relatively shifted to the upper side in the vertical direction and to the left side in the horizontal direction. In this case, weights are set as follows. Since the distance between Channel 1 in the upper left and the object is the shortest, the weight ($w_{amp}$) is made to be relatively large. Since the distance between Channel 3 in the lower right and the object is the longest, the weight ($w_{amp}$) is made to be relatively small. Furthermore, since the distances between Channel 4 in the upper right, Channel 2 in the lower left, and the object are halfway between both the distances, the weights ($w_{amp}$) are set to values halfway between both the distances.

As described above, in the fourth embodiment, distances between an object and each channel are determined based on a positioning image in order to set an objective function by determining weights ($w_{amp}$) of each channel based on the determined distances. Hence, the weights ($w_{amp}$) of each channel can be set accurately, which can improve an accuracy of an objective function. Consequently, SAR reduction as well as maintenance and improvement of $B_1$ distribution homogeneity can be achieved.

<<Fifth Embodiment>>

A fifth embodiment of the present embodiment will be described. The fifth embodiment is characterized by determining a weight ($w_{amp}$) of each channel using a SAR of each channel of the transmission coil.

In order to measure a SAR of each channel of the transmission coil, for example, the method of the literature (NEMA Standards Publication MS 8-2008) can be used. When a SAR of each channel measured using such a method is set as SAR(i)[i=1, 2, 3 . . . , ch], a weight ($w_{amp}$) of each channel can be determined as the following formula (5) for example.

$$w_{amp}(i) = q \times \frac{SAR(i)}{\sum_{i=1}^{ch} SAR(i)} \qquad (5)$$

Here, q is a proportional coefficient. That is, a weight ($w_{amp}$) of a channel whose SAR is relatively large is set greater than a weight ($w_{amp}$) of a channel whose SAR is relatively small.

Because a SAR of each channel varies depending on imaging conditions such as an imaging parameter value, an object attribute, and a disposition position of the object in a magnetic field space, it is basically desirable to measure each time these conditions vary. Alternatively, a SAR value of each channel according to the imaging conditions may be previously measured and stored in order to omit SAR measurement by selecting and using the stored value.

In any cases, the measured SAR of each channel varies according to a distance to an object. Specifically, a SAR of a channel disposed in a position close to the object tends to be greater than a SAR of a channel disposed in a position farther from the object. Therefore, by determining a weight ($w_{amp}$) of each channel as shown in FIG. 5, the weight ($w_{amp}$) of each channel tends to be different according to a distance to the object. That is, a weight ($w_{amp}$) of a channel disposed in a position relatively closer to the object is to be set greater than a weight ($w_{amp}$) of a channel disposed in a position relatively farther from the object.

Although configuration of each function of the RF shimming section 313 for realizing the fifth embodiment is similar to the configuration illustrated in the above FIG. 3, the processes of the following functional parts vary.

The condition storage part 304 previously stores a SAR value of each channel according to imaging conditions. Additionally, in a case of measuring a SAR of each channel of the transmission coil each time, it is unnecessary to store SAR values of the respective channels according to the imaging conditions.

The optimization condition setting part 302 measures a SAR of each channel of the transmission coil. Alternatively, a SAR value of each channel associated with imaging conditions substantially corresponding to imaging to be performed later is extracted from among SAR values of the respective channels according to the imaging conditions stored in the condition storage part 304. Then, based on the SAR value of each channel, a weight ($w_{amp}$) of each channel is determined, for example, as shown in the above formula (5) in order to set an objective function.

Also, although the process flow of the RF shimming section 313 is similar to that illustrated in the above FIG. 5, the processes of the following steps vary.

In Step S1004, the optimization condition setting part 302 measures a SAR of each channel of the transmission coil or, alternatively, extracts a SAR value of each channel associated with imaging conditions substantially corresponding to imaging conditions for imaging to be performed later from the condition storage part 304. Then, based on a SAR value of each channel, a weight ($w_{amp}$) of each channel is determined in order to set an objective function.

Because the other processes are similar to the process flow of FIG. 5, the description is omitted.

The following Table 1 shows an example of SARs measured with an object disposed in FIG. 10 using the four-channel transmission coil illustrated in FIG. 2 and an example in which a weight ($w_{amp}$) of each channel is determined using the above formula (5) based on the measurement result. In this case, it is set to be q=5,

TABLE 1

| CHANNEL | SAR (w/kg) | WEIGHT |
|---------|------------|--------|
| 1 | 0.35 | 1.75 |
| 2 | 0.25 | 1.25 |
| 3 | 0.15 | 0.75 |
| 4 | 0.25 | 1.25 |

As described above, by actually measuring or selecting a value from among SAR values of the respective channels for each of the imaging conditions that were prepared in advance, a SAR for each of the channels is acquired in order to determine a weight ($w_{amp}$) of each channel using these values in the fifth embodiment. Hence, a channel that greatly contributes to a SAR can be identified without acquiring a disposition position of an object, which can set an amplitude and a phase that are effective for each of the channels by SAR reduction.

REFERENCE SIGNS LIST

100: MRI apparatus
101: magnet
102: gradient magnetic field coil
103: object
104: sequencer
105: gradient magnetic field power source
106: high-frequency signal generator
107: table
108: receiver
109: calculator
110: display device
111: storage device
112: shim coil
113: shim power source
114: transmission coil
114-1: channel
114-2: channel
114-3: channel
114-4: channel
115: reception coil
117-1: electricity supply point
117-2: electricity supply point
117-3: electricity supply point
117-4: electricity supply point
200: phantom
201: imaging region
202: $B_1$ distribution
301: region setting part
302: optimization condition setting part
303: optimization part
304: condition storage part
310: imaging condition setting unit
311: imaging position setting section
312: static magnetic field shimming section
313: RF shimming section
320: main imaging unit
401: $B_1$ distribution
402: $B_1$ distribution
403: $B_1$ distribution
404: $B_1$ distribution
ROI 1: first region
ROI 2: second region

The invention claimed is:

1. A nuclear magnetic resonance imaging apparatus comprising:
a transmission coil having a plurality of channels that respectively transmit high frequencies (RF) to an object;
an RF shimming section determining at least one of an amplitude and a phase of the high frequencies to be transmitted respectively to a plurality of the channels as a high frequency magnetic field condition based on an objective function and a restriction condition so as to improve homogeneity of a high-frequency magnetic field ($B_1$) distribution that the transmission coil generates and to reduce a specific absorption ratio (SAR) of the object; and
a high-frequency signal generator generating the high frequencies for each of the channels based on the high frequency magnetic field condition,
wherein the RF shimming section determines objective function parameter values for each of the channels for setting the objective function according to contribution to the specific absorption ratio, and
wherein the objective function parameters includes a distribution weight (w), a weight ($w_{amp}$) of each of the channels, and an exponent (k),
the objective function is a linear combination in which a term showing reduction of the specific absorption ratio and a term showing improvement of the homogeneity are weighted with the distribution weight (w),
the term showing the reduction of the specific absorption ratio is formed by performing weighted addition for the exponential (the k-th power) of the amplitude of the high frequencies for each channel with the weight ($w_{amp}$), and
the RF shimming section determines the high frequency magnetic field condition as a solution that optimizes the objective function.

2. The nuclear magnetic resonance imaging apparatus according to claim 1,
wherein the RF shimming section determines a value of the weight ($w_{amp}$) of each of the channels according to contribution to the specific absorption ratio.

3. The nuclear magnetic resonance imaging apparatus according to claim 2, wherein the RF shimming section sets a weight ($w_{amp}$) of a channel whose contribution to the specific absorption ratio is relatively large so as to be greater than a weight ($w_{amp}$) of a channel whose contribution to the specific absorption ratio is relatively small.

4. The nuclear magnetic resonance imaging apparatus according to claim 2,
wherein the RF shimming section sets a weight ($w_{amp}$) of a channel disposed in a position relatively closer to the object so as to be greater than a weight ($w_{amp}$) of a channel disposed in a position relatively farther from the object.

5. The nuclear magnetic resonance imaging apparatus according to claim 3,
wherein the transmission coil has upper channels disposed on the upper side and lower channels disposed on the lower side in a magnetic field space, and
the RF shimming section sets weights ($w_{amp}$) of the lower channels so as to be relatively greater than weights ($w_{amp}$) of the upper channels.

6. The nuclear magnetic resonance imaging apparatus according to claim 3,
wherein the RF shimming section has a condition storage part that stores the objective function parameter values for each of the imaging sites and extracts a weight ($w_{amp}$) of each of the channels from the condition storage part according to an imaging site set by an operator and sets the weight.

7. The nuclear magnetic resonance imaging apparatus according to claim 1,
wherein the RF shimming section receives input of the objective function parameter values by an operator in order to set the objective function based on the input objective function parameter values.

8. The nuclear magnetic resonance imaging apparatus according to claim 4, comprising:
an imaging position setting section that acquires a positioning image in order to determine a position for imaging the object and determines a disposition position of the object in a magnetic field space based on the positioning image,
wherein the RF shimming section previously stores positions in which the respective channels of the transmission coil are arranged in the magnetic field space, evaluates distances between the object and each of the channels based on the object disposition position in the magnetic field space and the disposition positions of each of the channels in the magnetic field space, and then sets a weight ($w_{amp}$) of a channel disposed in a position relatively closer to the object so as to be greater than a weight ($w_{amp}$) of a channel disposed in a position relatively farther from the object.

9. A method for RF shimming in a nuclear magnetic resonance imaging apparatus that includes a transmission coil having a plurality of channels for respectively transmitting high frequencies (RF) to an object and a calculation unit performing RF shimming calculation that determines at least one of amplitudes and phases of the high frequencies to be transmitted respectively to a plurality of the channels so as to improve homogeneity of a high-frequency magnetic field distribution ($B_1$) generated by the transmission coil and to reduce a specific absorption ratio (SAR) of the object, the method comprising:
determining objective function parameter values for setting an objective function according to contribution to the specific absorption ratio for each of the channels during the RF shimming calculation based on the objective function and a restriction condition,
wherein the objective function parameter values includes a distribution weight (w), a weight ($w_{amp}$) of each of the channels, and an exponent (k),
the objective function is a linear combination in which a term showing reduction of the specific absorption ratio and a term showing improvement of the homogeneity are weighted with the distribution weight (w),
the term showing the reduction of the specific absorption ratio is formed by performing weighted addition for the exponential (the k-th power) of the amplitude of the high frequencies for each of the channels with the weight ($w_{amp}$), and
a weight ($w_{amp}$) of a channel whose contribution to the specific absorption ratio is relatively large is set so as to be greater than a weight ($w_{amp}$) of a channel whose contribution to the specific absorption ratio is relatively small.

10. The method for RF shimming according to claim 9, wherein a weight ($w_{amp}$) of a channel disposed in a position relatively closer to the object is set so as to be greater than a weight ($w_{amp}$) of a channel disposed in a position relatively farther from the object.

* * * * *